US00RE34387E

United States Patent [19]

Holmes et al.

[11] E Patent Number: Re. 34,387

[45] Reissued Date of Patent: Sep. 21, 1993

[54] METHOD FOR RESTORING DEPLETED PURINE NUCLEOTIDE POOLS

[75] Inventors: Edward W. Holmes; Judith L. Swain, both of Durham, N.C.

[73] Assignee: Duke University, Durham, N.C.

[21] Appl. No.: 167,325

[22] Filed: Mar. 11, 1988

Related U.S. Patent Documents

Reissue of:

[64] Patent No.: 4,575,498
Issued: Mar. 11, 1986
Appl. No.: 515,595
Filed: Jul. 21, 1983

[51] Int. Cl.[5] ..... A61K 31/70

[52] U.S. Cl. ..... 514/43; 536/28.8

[58] Field of Search ..... 514/43, 94

[56] References Cited

U.S. PATENT DOCUMENTS 3,332,935 7/1967 Yamazaki et al. ..... 536/23
3,803,126 4/1974 Rousseau et al. ..... 536/24

OTHER PUBLICATIONS

Toninello et al., *Chem. Abstr.*, 80, P57898(e) (1973).
Atsuta et al., *Chem. Abstr.*, 97, P124724(m) (1982).
Hasegawa et al., *Chem. Abstr.*, 100, P3950(d) (1984, effective date 1982).
Cohen et al., *Chem. Abstr.*, 100, P3958(n), effective date, 1983).
Lowy et al., Pediatr. Res., vol. 11, pp. 691-694 (1977).

*Primary Examiner*—Johnnie R. Brown
*Assistant Examiner*—L. Eric Crane
*Attorney, Agent, or Firm*—Richard F. Jenkins

[57] ABSTRACT

A method of increasing the rate of repletion of purine nucleotide pools in tissue deficient in the nucleotides, which comprises administering to a human or animal a therapeutically effective amount of 5-amino-4-imidazolecarboxamide riboside, 5-amino-4-imidazolecarboxamide, or a pharmaceutically acceptable salt thereof sufficient to increase the rate of the repletion is disclosed along with pharmaceutical compositions useful for carrying out the method of the invention.

6 Claims, 4 Drawing Sheets

METHOD FOR RESTORING DEPLETED PURINE NUCLEOTIDE POOLS

Matter enclosed in heavy brackets [ ] appears in the original patent but forms no part of this reissue specification; matter printed in italics indicates the additions made by reissue.

The investigations leading to the present invention were supported in part by Grant No. AM124135R23HL26831 from the Department of Health and Human Services of the National Institutes of Health and by a grant from the Howard Hughes Medical Institute.

BACKGROUND OF THE INVENTION

1. Field of the Invention

The present invention relates to methods of ameliorating damage caused by ischemia in myocardial tissue and other tissues.

2. Description of the Prior Art

Depletion of purine nucleotide pools is postulated to play a role in cardiac and skeletal muscle of dysfunction. A decrease in the total amount of adenine nucleoides and especially adenosine triphosphate (ATP) results from the insufficient energy supply available during low oxygen levels. Various methods have been proposed to protect the myocardium during anaerobic situations, both those resulting from disease or injury, such as myocardial infarctions and those deliberately induced, such as induced cardiac arrest without coronary perfusion for cardiac surgery. One of the methods intended to improve myocardial anoxic tolerance and to improve and accelerate post-anaerobic recovery is the administration of adenosine, as described in, for example Isselhard et al., Journal of Molecular and Cellular Cardiology, 12, 619-634 (1980). However, the various purine precursors, such as adenosine, inosine, and hypoxanthine which have previously been used to restore ATP levels have deleterious hemodynamic effects on the cardiovascular system. This is particularly true of adenosine which is known to have significant effects on heart rate, systemic blood pressure, cardiac output, and regional myocardial blood flow. Accordingly, new agents and methods of using them which provide the desired increase in the adenine nucleotide pool without deleterious effects on the cardiovascular system are needed.

SUMMARY OF THE INVENTION

It is an object of the present invention to provide a method for increasing the amount of purine nucleotides present in tissues.

It is a further object of this invention to provide a method of increasing the amount of purine nucleotides in ischemic and post-ischemic myocardial tissue without significantly affecting heart rate, systemic blood pressure, cardiac output, or regional myocardial blood flow.

These and other objects of the invention as will hereinafter become more apparent have been accomplished by providing a method of increasing the level of purine nucleotides in a tissue, which comprises administering to said tissue a therapeutically effective amount of 5-amino-4-imidazolecarboxamide riboside, 5-amino-4-imidazolecarboxamide, or a pharmaceutically acceptable salt thereof. The tissue may be present either in a human or animal body or may be maintained in a viable state outside the body.

While this invention is intended primarily for use in increasing purine nucleotide levels in myocardial tissues of mammals, the method can also be used with other intact organs, such as in organ preservation, especially preservation of kidneys. It can further be used in treating shock in which nucleotide pools of other organs become depleted, and it can be used in cerebral ischemia, such as following a stroke. The method may also be used in treating Lesch-Nyhan syndrome.

DESCRIPTION OF THE PREFERRED EMBODIMENTS

Figure 1A:
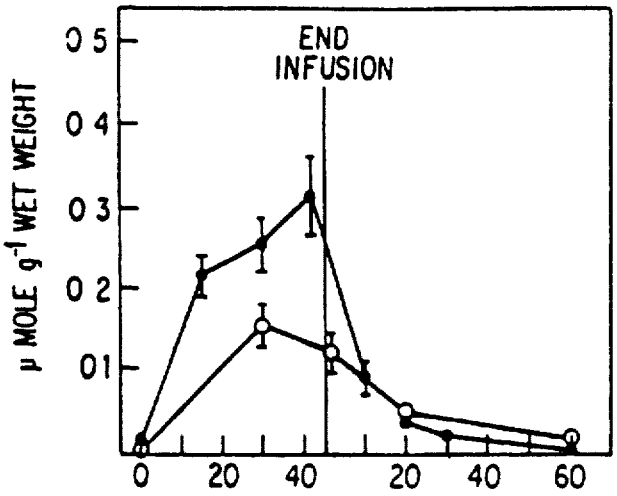

The present invention has arisen as a result of investigations conducted in the laboratories of the present inventors which indicate that the rate of purine nucleotide synthesis can be increased in a tissue deficient in the nucleotides by administering to the tissue a therapeutically effective amount of a compound of the invention. Some of these investigations have been previously published: (Sabina et al., Journal of Biological Chemistry; 17. 10178-10183 (1982) and Swain et al., Circulation Research, 51, 102-105 (1982). These publications are herein incorporated by reference.

Compounds useful in the method of the present invention are 5-amino-4-imidazolecarboxamide riboside (AICAriboside), 5-amino-4-imidazolecarboxamide (AICA) and pharmaceutically acceptable salts thereof. These compounds are represented by the formula

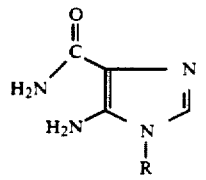

in which R is hydrogen or a $\beta$-D-ribofuranosyl group. AICA riboside and AICA are available commercially from Sigma Chemical Company, St. Louis, Mo., or may be synthesized by conventional techniques of organic chemistry, for example, as described in U.S. Pat. No. 3,919,192, which is herein incorporated by reference.

Generally, the desired imidazole derivative can be synthesized from adenine (for AICA) or adenosine for AICAriboside) by first forming the 1-N-oxide using the procedure of Posternak et al., Biochem. Biophys. Acta, 65, 558 (1962) by the action of excess m-chloroperbenzoic acid in sodium acetate. Alkylation of the N-oxide with methyl iodide in dimethyl sulfoxide yields the corresponding N-methoxide. Base-catalyzed hydrolysis at a pH of about 14 of the N-alkoxide followed by a spontaneous Dimroth rearrangement gives 5-amino-4-imidazolecarboxamide-O-methyloxime (or the corresponding riboside). Reduction by catalytic hydrogenation give the corresponding amidine, from which the carboxamide is obtained by hydrolysis.

The compounds of the invention can also be used in the form of phamaceutically acceptable salts, such as acid addition salts formsd from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, latate, maleate, methansulfonate, 2-naphthalenesulfonate, nicotinate, oxalate, polmitate, pectinate, persulfate, 3-phenylpropionate, picrate, pivalate, propionate, succinate, tartrate, thiocyanate, tosylate, and undecanoate. Of these salts, simple inorganic salts, such as salts of the hydrogen halides are preferred. AICA riboside and AICA themselves (i.e., not as salts) are particularly preferred.

Compounds of the inventive method may be used to treat any disorder of a functioning tissue or organ in which there is a depleted level of a purine nucleotide. Such depletion of purine nucleotide pools typically occur under ischemic conditions and are particularly prevalent in myocardial tissue during and after ischemia. Accordingly, a preferred embodiment of the present invention provides a method of increasing the rate of repletion of purine nucleotide pools in a tissue (particularly myocardial tissue) or organ deficient in said nucleotides by administering a compound of the invention to a human or animal suffering from such a condition, where the amount of active ingredient administered is sufficient to increase the rate of repletion.

Although this invention and its preferred embodiments are primarily addressed to use in humans, veterinary use is also encompassed by the invention. In this regard, an active ingredient may be administered to increase the rate of repletion in a tissue present in, for example, dogs, cats, horses, cattle and sheep. Administration to laboratory animals, such as mice and rats, in order to prevent damage caused by depleted purine nucleotide pools while experimental work is being carried out (especially if the experimental work involves surgery), is also contemplated. The examples are not intended to be limiting but are merely illustrative of veterinary use.

The tissue in which repletion is to take place is likewise not limited although increasing rate of repletion in myocardial tissue is preferred. Other tissues in which repletion of purine nucleotide pools is important include kidney, brain, skeletal, muscle, liver, and gastrointestine.

Furthermore, since the method of the invention is useful in maintaining the proper functioning of any tissue or organ under ischemic conditions, another preferred embodiment involves administering compounds of the invention to a functioning tissue or organ maintained outside a human or animal body. Thus, the method is particularly useful both in maintaining organs in a functioning state outside a body and in organ transplantation, particularly kidneys, hearts, and livers. In this context, the term "functioning organ" means an organ or part of an organ removed from a human or animal and maintained in a viable state outside the body. The organ need not be complete, since, for example, transplantation of a partial organ, such as a pancreas, may occur, but must be capable of functioning with its intended purpose after transplantation.

Compounds of the invention are administered to the affected tissue at the rate of from 0.1 to 2.0 μmole/min/kg, preferably from 0.2 to 1.0 μmole/min/kg, and most preferably about 0.5 μmole/min/kg. Such rates are easily maintained when the preferred methods of administration (directly to the blood supply of the tissue as discussed below) are used. When other methods are used (e.g., oral administration), use of time-release preparations to control the rate of release of the active ingredient is preferred.

For the purposes of the invention, the compounds of the invention may be administered orally, parenterally, by inhalation spray, or rectally in formulations containing conventional non-toxic phamaceutically acceptable carriers, adjuvants and vehicles. The term parenteral as used herein includes subcutaneous intravenous, intramuscular, and intraarterial injections and infusion techniques. Intraarterial and intravenous injection as used herein includes administration through catheters. Preferred are methods of administration which allow rapid access to the tissue or organ being treated, such as intravenous injections for the treatment for myocardial infarction. When an organ outside a body is being treated perfusion is preferred.

Pharmaceutical compositions containing the active ingredient may be in any form suitable for the intended method of administration. When used for oral use, for example, tablets, troches, lozenges, aqueous or oil suspensions, dispersible powders or granules, emulsions, hard or soft capsules, syrups or elixers may be prepared. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate along or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservative such as ethyl or n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or cocunut oil, or in a mineral oil such as liquid paraffin. The oil suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservative. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters of partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The amount of active ingredient that may be combined with the carrier material to produce a signle dosage form will vary depending upon the host treated and the particular mode of administration. For example, a time-release formulation intended for oral administration to humans may contain 20 to 200 μmoles of active material compounded with an appropriate and convenient amount of carrier material which may vary from about 5 to about 95% of the total composition. It is preferred that pharmaceutical compositions be prepared which provides easily measureable amounts for administration. For example, an aqueous solution intended for intravenous infusion should contain from about 20 to about 50 μmoles of the active ingredient per milliliter of solution in order that infusion of a suitable volume at a rate of about 30 ml/hr can occur.

It will be understood, however, that the specific dose level of any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occulusion. The compound would be given as a sterile injectable preparation with water or isotonic sodium chloride as the solvent. The solution can be administered directly into the coronary artery at the time of left heart catheterization and intracoronary thrombolytic therapy. The rate of administration could vary from 0.2 to 1 μmole/min/kg with, for example, an infusion volume of 30 ml/hr. Duration of therapy would typically be about 24 hours.

Angina and early myocardial infarcts can be treated by intravenous administration using a sterile injectable preparation using the rates discussed above.

Compounds of the invention can also be administered to patients intravenously during cardiac bypass surgery. The compound can be added directly to the solution administered by the membrane oxygination, or to the cardiac preservation solution, at the rates discussed above.

Organs can be preserved using the method of the invention by perfusing the organ with a solution containing a compound of the invention. The dosage administered would vary with the rate of perfusion of the organ, as is well understood to those skilled in the art. This method is particularly applicable to organs and tissues used in organ transplantation.

Lesch-Nyhan Syndrome, an inherited disorder caused by a dificiency of the enzyme hypoxanthine-guanine phosphoribosyl transferase which is x-linked and causes severe neurological disease, gout, and kidney stones, can be treated using the method of the invention. Oral administration is preferred because of the long term nature of the disorder.

Of the previously mentioned treatments, treatment of coronary occulsion, early myocardial infarcts, and angina and use in organ transplantation and preservation are preferred.

A particularly preferred embodiment of the invention is used in patients undergoing thrombolytic therapy during coronary occulsion. At the present time thrombolytic therapy is accomplished by positioning a catheter in the orifice of the involved coronary artery and then infusing a thrombolytic agent directly into the coronary artery. Following thrombolysis, a compound of this invention would be infused directly into the coronary artery by the catheter already in place. An appropriate dose would be, for example, 0.5 μmole/-min/kg. After an initial period of time (e.g. 20 min–1 hr.), the infusion would be switched from intracoronary to intravenous administration and continued for 24 hours.

The invention now being generally described, the same will be better understood by reference to certain specific examples which are included herein for purposes of illustration only and are not intended to be limiting of the invention or any embodiment thereof, unless so specified.

EXAMPLE 1

Metabolism of AICA riboside in Normal Myocardium Experimental Procedures

Animal Preparation—Seven adult mongrel dogs were anesthetized intramuscularly with 40 mg of morphine sulfate and intravenously with 80 mg/kg of chloralose, an endotraceal tube was inserted, and ventilation was maintained with an Emerson volume-cycled respirator and 100% oxygen. The heart was exposed through a left lateral thoracotomy, polyvinyl chloride catheters (3-mm outer diameter) were inserted into the left atrium and into the aorta through the right femoral artery, and a Statham TTQ electromagnetic flow meter probe was positioned around the ascending aorta. The aortic pressure catheter was connected to a Statham P23 Db transducer (Statham Instruments, Inc., Oxnard, Calif.) with the zero reference at the midchest level. Aortic flow was measured with a Howell Instruments Series 1000 Flowmeter, and stroke volume and cardiac output were calculated from the aortic flow measurement. All hemodynamic data were monitored continuously throughout the course of the study. In 5 of the animals, the skin of the left dorsal hindlimb was opened and the gastrocnemius muscle was identified for subsequent tissue sampling.

After hemodynamic parameters had stabilized, regional myocardial blood flow was measured by injecting radioactively labled microspheres. Tissue samples were obtained from the left ventricle and from the left gastrocnemius muscle. A venous blood sample was also obtained. AICAriboside (100 mM) was then infused into the left atrium at 1.9 ml/min. Repeat tissue samples were taken from the left ventricle at 15, 30 and 42 min. of infusion, and tissue samples were taken from the gastrocnemius muscle at 30 min. of infusion. Venous and arterial blood samples were also obtained at 42 min. of infusion, and regional myocardial blood flow was measured at 10 and 39 min. of AICAriboside infusion. AICAriboside infusion was terminated after 42 min., and tissue samples were taken from the left ventricle at 10, 20, 30 and 60 min. postinfusion and from the left gastrocnemius muscle at 2,22 and 60 min. postinfusion. Venous blood samples were obtained at 10, 30 and 60 min. after AICAriboside infusion. In 4 of the 7 dogs, 400 mM formate was infused intravenously at the rate of 1.9 ml/min. for 42 min. prior to and during AICAriboside infusion. These same animals also received 6 mg of folinic acid as an intravenous bolus 30 min. prior to and 15 min. after initiating AICAriboside infusion.

Tissue-sampling Procedure—Myocardial tissue samples of 10–40 mg. wet weight, were obtained from the free wall of the left ventricle using a high speed rotary drill (Emesco 12,000-rpm bench engine equipped with a Doriot Handpiece, Teledyne Emesco, Englewood, N.J. and Healthco, Inc., Boston, Mass.) and a 2-mm outer diameter hollow drill bit. Each successive sample was taken proximal to the preceding one with respect to blood flow. The tissue samples were blotted on a saline sponge to remove excess blood and were compressed between metal tongs precooled in liquid nitrogen. The time required for myocardial sampling and freezing encompassed less than 10s. Skeletal muscle (gastrocnemius) samples weighing 20–50 mg were obtained by compressing part of the exposed muscle between metal tongs precooled in liquid nitrogen and excising frozen tissue with a scalpel. The frozen tissue samples were then plunged immediately into liquid nitrogen, where they were stored until the sample could be processed for determination of nucleotide, nucleoside, base, and creatine phosphate content.

Analysis of Tissue Samples—Prior to weighing, the skeletal muscle samples were trimmed of any excess tissue that was not compressed between the frozen tongs. Each frozen sample was then weighed to the nearest 0.05 mg at room temperature. Weighing was performed in less than 10s to ensure that no catabolism of high energy phosphate occurred during this period. The tissue was then added directly to a glass tissue grinder containing 0.5 ml of cold (4° C.) 12% trichloroacetic acid. Extraction was carried out at 4° C. for 30 min. with periodic grinding of the muscle until a homogeneous slurry was produced. Following centrifugation at 4° C. for 2 min. at 5000×g, the supernatant was mixed with intermittent agitation at room temperature for 1 min. with 10 ml of 0.5M tri N-octylamine in Freon to remove the acid. After centrifugation at 2000×g for 2 min. at 4° C., the aqueous layer was removed for analysis. The supernatant was passed through a 0.45 μ filter before injection onto the high performance liquid chromatograph.

Nucleotide analyses were carried out as follows. A 50-μ sample of the muscle extract was injected onto a Whatman Partisil-10 SAX anion exchange column (25 cm×4.6 mm 10-μm particle size) using a gradient of 5 mM $NH_4H_2PO_4$ pH 2.8 (Buffer A) and 750 mM $NH_4H_2POI_4$, pH 3.9 (Buffer B) at a flow rate of 2.0 ml/min. A linear gradient was developed over 40 min. at 0% Buffer B to 100% Buffer B. A Waters Model 440 high pressure liquid chromatograph equipped with a Model 660 solvent programmer and data module was used. The various peaks in the extracts were identified by comparison for retention times with known external standards and relative absorbance at 254/280 min. The following nucleotides were routinely quantified in the muscle extracts: ATP, ADP, AMP. AICAR, IMP. $NAD^+$, GDP, GTP, UTP and CTP. The results were expressed as μmol or mmol/g wet weight.

Nucleosides and bases (adenosine, inosine, and hyopxanthine) were separated on a Waters C-18 reversephase column (30 cm×3.9 mm) using a gradient of Buffer C (60 mM $K_2HPO_4$, 40 mM $KH_2PO_4$ adjusted to pH 6.0 with concentrated phosphoric acid) and Buffer D (Buffer C in 25% methanol (v/v)) at a flow rate of 1.5 ml./min. The column was developed over 40 min. using a nonlinear gradient of 0% Buffer D to 100% Buffer D (% pump Buffer D=100 (time(min)/40)). The results were expressed in nmol/g, wet weight. AICAriboside, not separable from AMP under the above conditions, was quantitated on the same column using a gradient of Buffer E (20 mM $KH_2PO_4$, pH 5.6) and Buffer F (methanol:water (60:40)(v/v)) at a flow rate of 1.5 ml/min. A linear gradient with initial conditions of 6% Buffer F and final conditions of 40% Buffer F was developed over 35 min. Results were expressed as nmol/g, wet weight.

The same extract used for nucelotide, nucleoside, and base analyses was also used for creatine phosphate determination. Twenty-five microliters of extract were mixed with 25 μl of 100 mM Tris-HCl buffer, pH 7.4, which contained 4.0 mM [$^{14}$C]ADP (2.5 μCi/μmol), 10 mM $MgCl_2$, and 1.6 units of creatine phosphokinase. After incubation at 37° C. for 30 min. a 5-μl aliquot of the reaction mixture was applied to a polyethyleneimine cellulose F TLC plate and was developed in 0.8M $LiCl_2$ for 80 min. The ATP spot was identified by UV light, cut out, and counted at 79% efficiency in Triton scintillation fluid using a Pakcard Tri-Carb liquid scintillation spectrometer. Creatine phosphate content was calculated from the amount of ATP produced in this reaction. The results were expressed as μmol/g, wet weight.

Preparation and Assay of Adenylosuccinate Lyase—Six-week-old C57BL/6J mice were killed, and the hearts and gastrocnemius muscles were excised, weighed, and homogenized to a slurry in 4 volumes of 50 mM Tris-HCl, pH 7.4 at 25° C. containing 1 mM EDTA and 1 mM β-mercaptoethanol in a TenBroeck glass homogenizer. The homogenate was centrifuged at 10,000×g for 15 min and the supernatant was dialyzed against 1,000 volumes of the extraction buffer for 2 h at 4° C. The lyase activity was partially stabilized by the addition of EDTA and β-mercaptoethanol, but some activity was lost even on storage at −70° C.

The assays were carried out at pH 7.4 were reaction mixtures that contained 50 mM Tris-HCl buffer, 1 mM EDTA, 1mM β-mercaptoethanol, 20 μM adenylosuccinate, and the enzyme extract (protein concentration, 0.13–0.20 mg/ml). The decrease in absorbance at 280 nm was measured using a Gilford recording spectrophotometer. All assays were done at 25° C. and were linear with respect to time of incubation and with the amount of protein in extract added to the assay.

Other Methods—Serum urate was determined by the enzymatic spectrophotometric method as previously described in Liddle et al., J. Lab. Clin. Med., 54, 909–913 (1959).

All results are expressed as the mean ±S.E. A paired t test was used when comparing changes within cardiac or with skeletal muscle in individual animals, and an unpaired t test was used when comparing changes between cardiac and skeletal muscle.

Material—All nucelotides, nucleosides, bases, creatine phosphate, and creatine phosphokinase were purchased from Sigma. Other compounds were the highest grade commercially available [$^{14}$C]ADP (521 μCi/μmol) was purchased from Amersham Corp. Polyethyleneimine cellulose plates were obtained from MC/B Manufacturing Chemists, Inc., Cincinnati, Ohio. C57BL/6J mice were purchased from Jackson Laboratories.

Results

AICAriboside Uptake—AICAriboside concentration was too low to be detected in plasma from control animals, but after 42 min of AICAriboside infusion, the plasma concentratin reached 336±26 μm. FIG. 1A illustrates the time course for accumulation and disappearance of AICAriboside in cardiac and skeletal muscle. As in plasma, muscle content of this nucleotide precursor was too low to be detected in control samples, but after 15 min of infusion. AICAriboside was readily detected in cardiac and skeletal muscle. The content of AICAriboside in these tissues increased throughout the period of infusion. The mean content of AICAriboside in cardiac muscle was 66% greater than that of skeletal muscle after 30 min of infusion. Once infusion was stopped, AICAriboside concentration fell rapidly in both tissues, with the rate of decline being greater in cardiac muscle.

Figure 1B:
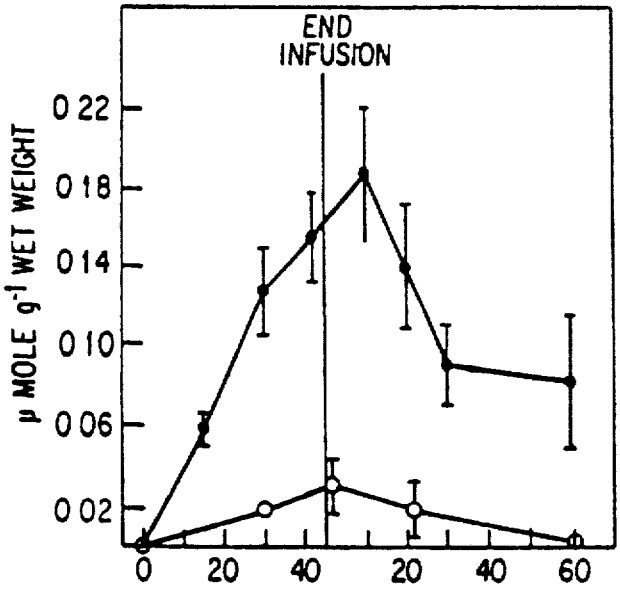

Formation of 5-Amino-4-imidazolecarboxamide Ribotide (AICAR)—AICAR, an intermediate in the de novo pathway and the direct product of AICAriboside phosphorylation, was not present in sufficient quantities to be detected in control samples of cardiac or skeletal muscle. However, during AICAriboside infusion, AICAR content increased progressively in both tissues (FIG. 1B). The time course for accumulation of AICAR in these two tissues was similar to that of its precursor. AICAriboside, except AICAR peaked minutes after AICAriboside infusion was stopped. As with AICAriboside, AICAR accumulation was also greater in cardiac muscle. The maximum content attained in cardiac muscle was 0.188±0.034 μmol/g, wet weight, compared to 0.032±0.013 μmol/g, wet weight, in skeletal muscle.

In an attempt to enhance the conversion of AICAR to IMP, folate and formate were added to the infusate in 4 to 7 dogs. The amount of these one-carbon sources did not affect the amount of AICAR which accumulated, the extent to which the nucleotide pools were expanded, or the flux through the purine pathway as evidenced by the amount of urate produced. Consequently, the folate-formate-treated dogs were included in the analyses with the dogs that did not receive folate and formate.

Effect on IMP Concentration—IMP, the first complete purine nucleotide synthesized in the de novo pathway, is the next stable intermediate formed after AICAR, and it is located at an important branchpoint in the pathway. Basal concentrations of IMP were found to be 6 (range 3–17) and 7 (range 3–18) nmol/g, wet weight, in cardiac and skeletal muscle, respectively. Tables I and II demonstrate that IMP content increased significantly in both tissues with AICAriboside infusion. Unlike AICAriboside and AICAR, IMP accumulation was not progressive throughout the infusion, IMP content reached its maximum at the earliest time point samples were taken and remained elevated throughout the course of the experiment. In contrast to the results obtained for AICAriboside and AICAR, the increase in IMP content was consistently greater in skeletal muscle. IMP content rose 6–7 fold in skeletal muscle, compared with a 3–4 fold increase in IIMP content of cardiac muscle.

TABLE I

| Effect of AICAriboside administration on purine metabolism | | | | |
|---|---|---|---|---|
| | AICAriboside infusion (mm) | | | |
| | Control | 15 | 30 | 42 |
| | μmol/g. wet weight | | | |
| Cardiac muscle metabolites | | | | |
| AMP | 0.060 ± 0.009 | 0.056 ± 0.008 | 0.050 ± 0.005 | 0.053 ± 0.007 |
| ADP | 0.79 ± 0.04 | 0.77 ± 0.06 | 0.82 ± 0.03 | 0.77 ± 0.03 |
| ATP | 5.55 ± 0.17 | 5.77 ± 0.24 | 5.89 ± 0.16[a] | 5.77 ± 0.28 |
| TAN | 6.40 ± 0.19 | 6.59 ± 0.29 | 6.77 ± 0.16[a] | 6.59 ± 0.27 |
| IMP | 0.006 ± 0.002 | 0.020 ± 0.007 | 0.030 ± 0.021 | 0.019 ± 0.006[a] |
| Ino | 0.009 ± 0.002 | ND | 0.012 ± 0.001 | ND |
| Hyp | 0.003 ± 0.002 | ND | 0.013 ± 0.006 | ND |
| | mg/dl | | | |
| Serum urate concentrations | | | | |
| Urate | 0.096 ± 0.09 | ND | ND | 3.5 ± 0.4[a] |
| | Postinfusion | | | |
| | 10 | 20 | 30 | 60 |
| | μmol/g. wet weight | | | |
| Cardiac muscle metabolites | | | | |
| AMP | 0.054 ± 0.007 | 0.054 ± 0.005 | 0.055 ± 0.006 | 0.052 ± 0.006 |
| ADP | 0.83 ± 0.05 | 0.81 ± 0.04 | 0.84 ± 0.03 | 0.82 ± 0.04 |
| ATP | 6.07 ± 0.17[a] | 5.83 ± 0.14[a] | 5.98 ± 0.07[a] | 5.72 ± 0.27 |
| TAN | 6.96 ± 0.20[a] | 6.70 ± 0.10[a] | 6.87 ± 0.10[a] | 6.59 ± 0.24 |
| IMP | 0.018 ± 0.003[a] | 0.017 ± 0.005 | 0.016 ± 0.003[a] | 0.017 ± 0.003[a] |
| Ino | 0.009 ± 0.001 | 0.007 ± 0.001 | 0.009 ± 0.002 | 0.006 ± 0.001 |
| Hyp | 0.016 ± 0.008 | 0.007 ± 0.002 | 0.003 ± 0.002 | 0.001 ± 0.001 |
| | mg/dl | | | |
| Serum urate concentrations | | | | |
| Urate | 3.5 ± 0.5[a] | ND | 2.9 ± 0.2[a] | 2.40 ± 0.4[a] |

Results expressed as mean ± S.E., n = 7. ND, not determined. Ino, inosine; Hyp, hypoxanthine.
[a]Indicates P < 0.005 compared to control.

TABLE II

| Changes in skeletal muscle metabolited produced by AICAriboside administration | | | | | |
|---|---|---|---|---|---|
| | AICAriboside infusion (min) | | Postinfusion (min) | | |
| | Control | 30 | 2 | 22 | 60 |
| AMP | 0.010 ± 0.003 | 0.016 ± 0.009 | 0.016 ± 0.002 | 0.014 ± 0.003 | 0.018 ± 0.007 |
| ADP | 0.05 ± 0.04 | 0.53 ± 0.04 | 0.65 ± 0.06[a] | 0.59 ± 0.03 | 0.56 ± 0.05 |
| ATP | 3.89 ± 0.33 | 3.92 ± 0.23 | 4.68 ± 0.45[a] | 4.34 ± 0.21 | 3.60 ± 0.41 |
| TAN | 4.41 ± 0.36 | 4.47 ± 0.27 | 5.34 ± 0.51[a] | 4.94 ± 0.23 | 4.18 ± 0.44 |
| IMP | 0.007 ± 0.003 | 0.050 ± 0.012[a] | 0.046 ± 0.012[a] | 0.045 ± 0.016[a] | 0.043 ± 0.015[a] |
| Ino | 0.006 ± 0.002 | 0.035 ± 0.009[a] | 0.024 ± 0.008 | 0.024 ± 0.011 | 0.055 ± 0.031 |
| Hyp | 0.006 ± 0.003 | 0.024 ± 0.007[a] | 0.022 ± 0.009 | 0.021 ± 0.008 | 0.041 ± 0.017 |

Results expressed as mean ± S.E.s, n = 5. Ino, inosine; Hyp, hypoxanthine.
[a]Indicates P < 0.05 compared to control.

Effect of AICAriboside Infusion on Other Nucleotide Pools—Tables I and II also illustrate the response of the total adenine nucleotide (TAN=ATP+ADP+AMP) pool to AICAriboside infusion. In cardiac tissue, significant increases in TAN were observed within 30 min of infusion and persisted for 30 min after the infusion was stopped. TAN in heart muscle increased from a basal concentration of 6.40±0.20 μmol/g to a maximum of 6.96±0.20 μmol/g, wet weight ($p<0.005$). Individual analyses of AMP, ADP, and ATP demonstrated that expansion of the TAN pool in cardiac tissue was due almost entirely to an increase in the content of ATP from 5.55±0.17 to 6.07±0.17 μmol/g, wet weight ($p<0.02$). AMP and ADP did not change significantly at any time point. Additionally, the adenylate energy charge (AEC=(½ADP+ATP)/(AMP+ADP+ATP)) was 0.929±0.003 in cardiac muscle before AICAriboside infusion, and the energy charge did not vary during the course of the experiment. Similar trends in ATP and TAN content of skeletal muscle were observed during AICAriboside infusion, but the changes were not statistically significant at all time points because of the fewer number of samples and greater variability in nucleotide content.

Adenylosuccinate was not detectable in any biopsies taken before, during or after AICAriboside infusion. The lower limit of detection for this nucleotide with the techniques used in this study is 3 nmol/g, wet weight, a value which is higher than that reported to be present in resting skeletal muscle in the rat.

Guanine nucleotide content of cardiac muscle was only 3.5% of the adenine nucleotide content. GMP content was too low to be accurately determined with the technique used here (<2 nmol/g, wet weight). The guanine nucleotide content, as reflected by change in GDP+GTP, tended to increase in cardiac muscle throughout the course of the experiment (data not shown). Due to the variability in quantitating these compound, statistical significant was only attained at one time point. Nevertheless in 6 to 7 dogs, the guanine nucleotide pool remained elevated for up to 60 min after AICAriboside infusion was discontinued. In skeletal muscle, guanine nucleotide content tended to increase as well, but the even lower content of these nucleotides in this tissue, i.e. 40% of that in cardiac muscle, obviated the demonstration of statistically significant changes.

Figure 2:
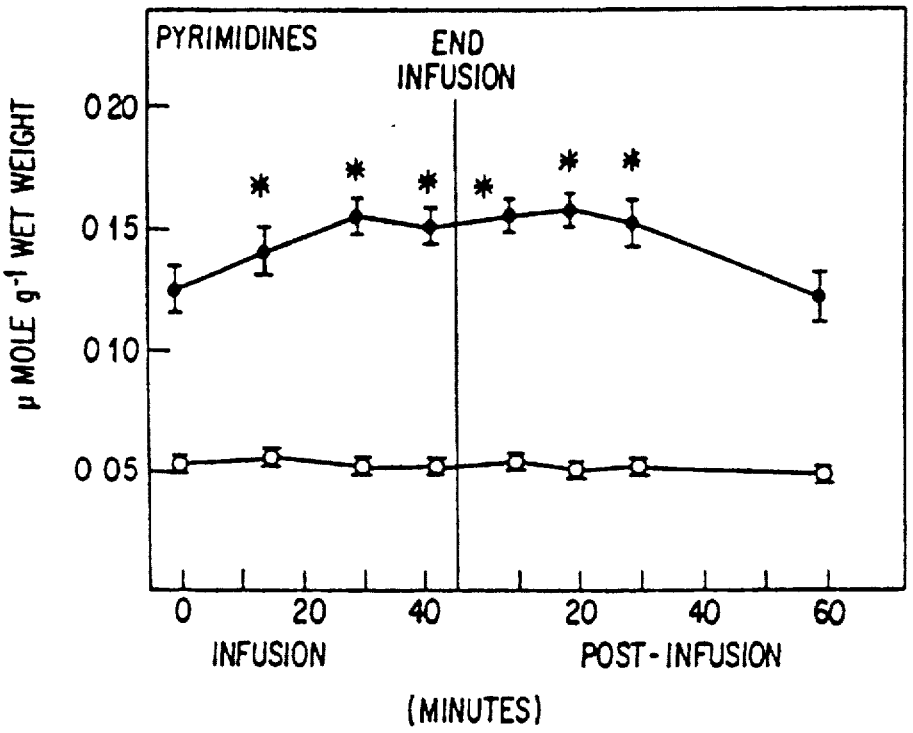

FIG. 2 illustrates the changes observed in the pyrimidine nucleotide pools in cardiac muscle following AICAriboside infusion. The magnitude of expansion of the UTP pool was even greater than that of the ATP pool during AICAriboside infusion. UTP content rose from a basal level of 0.126±0.009 to a maximum of 0.157±0.006 μmol/g, wet weight ($p<0.005$). There was no detectable change in myocardial content of CTP. The response of the pyrimidine pool in skeletal muscle was similar to that in the myocardium, but the lower content of pyrimidine nucleotides, i.e. 60% of cardiac muscle, and greater variability in quantitation of these pools in skeletal muscle prevented the demonstration of statistical significance (data not shown).

The content of $NAD^+$ did not vary in either heart or skeletal muscle throughout the period of infusion, being 0.64±0.01 and 0.32±0.04 μmol/g, respectively.

Effects of AICAriboside Infusion on Creation Phosphate—The creatine phosphate content of cardiac and skeletal muscle was 6.8±0.4 and 10.6±0.5 μmol/g, wet weight, respectively, at the beginning of the study and did not vary significantly throughout the course of the study.

Products of Purine Catabolism—The basal content of inosine was 9 (range 5–17) and 6 (range 2–10) nmol/g, wet weight, in cardiac and skeletal muscle, and the content of hypoxanthine in these tissues was 3 (range 1–6) and 6 (range 1–13) nmol/g, wet weight. Tables I and II illustrate the changes observed in cardiac and skeletal muscle content of inosine and hypoxanthine during the course of the experiment. Throughout the infusion of AICAriboside and up to 60 min thereafter, the content of inosine and hypoxanthine was consistently elevated in skeletal muscle. Both catabolites were increased in skeletal muscle in all animals at every time point, except 60 min postinfusion where all but one of the animals exhibited an increase. In contrast, myocardial content of the membrane-permeable inosine and hypoxanthine was only minimally increased throughout the course of the study. This could be attributed to the higher blood flow in cardiac muscle relative to resting skeletal muscle.

Adenosine did not increase in either cardiac or skeletal muscle during AICAriboside infusion (data not shown).

Table I also lists the changes in serum urate concentration observed during the course of the study. The mean serum urate concentration increased 3.7-fold following the infusion of 8 mmol of AICAriboside.

Alternate Pathway of AICAriboside Metabolism—The finding of a new peak only in the chromatographs obtained from biopsies taken after AICAriboside infusion suggests that this new compound is a previously unrecognized AICAriboside metabolite. Several lines of evidence support the identification of this new peak as AICAriboside-TP. First, in the chromatographic system used in this study, nucleotides elute in groups based on the relative state of phosphorylation, such that monophosphates elute sooner than diphosphates and diphosphates elute sooner than triphosphates with no overlap of the groups. The new peak eluted after the ATP peak, suggesting it was triphosphate. Second, the 280/254 absorption ratio suggested that the new peak contained 5-amino-4-imidazolecarboxyamide. The absorbance ratios for standard solutions of 5-(4)-amino-4-(5)-imidazolecarboxyamide (0.88±0.02), AICAriboside (0.78±0.02), and AICAR (0.82±0.02) are similar to that of the new peak (0.76±0.03). Third, the new peak was observed only in chromatographs of cardiac and skeletal muscle samples taken during and after infusion of AICAriboside. The size and time of appearance of this peak in both tissues correlated with the relative amounts of AICAR which accumulated in each tissue. In the animal accumulating the most AICAR in cardiac tissue, this peak appeared soon after initiation of AICAriboside infusion and was larger than in any other animal. In the animals accumulating the least AICAR in cardiac tissue, the new peak appeared only in later tissue samples and was smaller than in any other animal. Tissue samples from other animals were intermediate in both time of appearance and size of this new peak. The relationship between AICAR accumulation and the appearance of a suspected triphosphate of AICAriboside has also been observed in adenine auxotrophs of Neurospora crassa, which accumulate AICAR due to a genetic block in the purine de novo pathway.

Figure 1C:
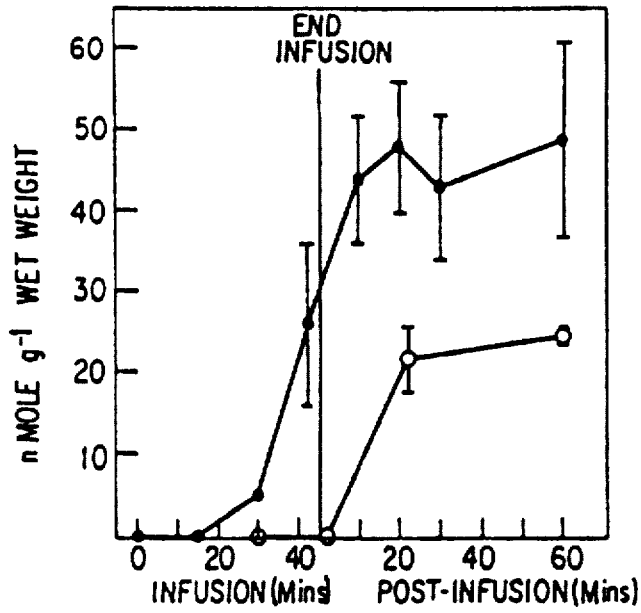

Attempts to synthesize AICAriboside-TP from the monophosphate using myokinase have not been successful, and since no standard for this compound is available, AICAriboside-TP content of the biopsies was quantitated on the assumption that the extinction coefficient of the triphosphate is similar to that of AICAR (i.e. $E\lambda_{280}=8800$). FIG. 1C illustrates changes in the content of this compound in cardiac and skeletal muscle during the course of the experiment. As with AICAriboside and AICAR, the accumulation of AICAriboside-TP was greater in cardiac muscle.

Inhibition of Adenylosuccinate Lyase by AICA-R—The apparent $K_m$ of adenylosuccinate lyase for adenylososuccinate was determined to be 2.2±0.3 μM and 4.5±1.5 μM for the cardiac and skeletal muscle enzymes, respectively. These are average values for experiments with 4 separate enzyme preparations. The experimental points in the double reciprocal plots were fitted to the best line by the method of least squares with all points being weighted equally. Using Dixon plots, $K_i$ values for AICAR of 4.5±1.7 μM and 7.6±3.2 μM were obtained for the cardiac and skeletal muscle enzymes, respectively.

Hemodynamic and Blood Flow Measurements—Heart rate, aortic systolic and diastolic pressure, cardiac output, and epicardial and endocardial regional blood flow were not significantly altered during AICAriboside infusion (data not shown).

Discussion

This study provides a number of insights into AICAriboside and purine metabolism in cardiac and skeletal muscle. This compound of the invention readily diffuses from plasma into the interstitial space and intracellular compartments as evidenced by the similar concentrations of AICAriboside in plasma and in myocardium. The lower AICAriboside concentration in skeletal muscle relative to that in myocardium appear to reflect the lower blood flow of resting skeletal muscle compared to that of the heart. Once in the myocyte, AICAriboside is metabolized to the ribotide.

AICAR accumulated in greater concentrations than any other purine monophosphate following AICAriboside infusion. Although the inventors do not wish to be limited by theory, the accumulation of AICAR suggests that either the activity of 10-formyltetrahydrofolate:5'-phosphoribosyl-5-amino-4-imidazolecarboxamide formyltarnsferase (EC 2.1.2.3) is limiting for 5-formamido-4-imidazolecarboxamide ribotide synthesis or that the other substrate for this reaction, 10-formyltetrahydrofolate, is limiting. Although 10-formyltetrahydrofolate levels were not measured, the concomitant administration of the precursors tetrahydrofolate did not affect the extent to which AICAR accumulated. This result suggests that the activity of the formyltransferase in myocytes may not be great enough to handle the marked increase in flux through the distal reactions of the pathway produced by the administration of AICAriboside.

A significant proportion of the AICAR produced by AICAriboside is metabolized to IMP as evidenced by the increase in the intracellular content of IMP and other purine nucleotides and by the striking increase in serum urate concentration. When the results of a number of the experiments in this metabolism study are considered together, it appears that a small proportion of the newly synthesized IMP follows the anabolic route toward adenine nucleotides as evidenced by the increase in myocyte ATP content. However, a much greater proportion of the newly synthesized IMP is channeled through the catabolic route as evidenced by the striking increase in serum urate concentration. Of the 8 mmol of AICAriboside infused, at least 25% is metabolized to purine nucleotides, which in turn are subsequently catabolized during the 42 min of infusion. A minimal estimate of the amount if AICAriboside metabolized to purine nucleotide and subsequently catabolized was obtained by multiplying the increase in serum urate concentration by the volume in which rate was distributed. The latter was assumed to equal total body water. This calculation is a conservative estimate of the increase in nucleotide synthesis and catabolism since it fails to take into account that a significant amount of urate is oxidized to allantoin in the mongrel dog and that a portion of the urate formed from AICAR is excreted by the kidney during the course of the infusion.

One explanation for the diversion of most of the newly synthesized IMP into the catabolic pathway may be the consequence of an unusual property of adenylosuccinate lyase. This protein is a bifunctional enzyme which not only catalyzes the displacement reaction leading to AMP synthesis from adenylosuccinate, but it also catalyzes AICAR synthesis in the usual sequence of reactions in the de novo pathway. Both of the lyase activities of this bifunctional enzyme are inhibited by AICAR. In the present study, the maximal concentrations of AICAR attained in cardiac ($813\pm147$ $\mu$M) and skeletal muscle ($140\pm57$ $\mu$M) was found to exceed the $K_i$ value of adenylosuccinate lyase from these tissues by 180- and 18-fold, respectively. In addition to this effect of AICAR on adenylosuccinate lyase activity, the modest expansion of the adenylate and guanylate pools produced by AICAriboside infusion may have inhibited adenylosuccinate synthetase and inosinic acid dehydrogenase. The combination of thse effects of AICAriboside administration may account for the shunting of newly synthesized IMP toward inosine formation.

The effects of AICAriboside administration are not limited to changes in purine metabolism. In myocardial cells, the UTP pool increased by 25% following AICAriboside infusion. Since there is no reason to think that AICAriboside metabolism per se would affect UTP utilization, the most straightforward explanation for the increase in UTP concentration is an increase in the rate of synthesis of this pyrimidine nucleotide. Prior studies with cell culture models have suggested a coordination between purine and pyrimidine nucleotide synthesis and results of these metabolic experiments are consistent with this hypothesis. Although the biochemical bases for coordinate regulation of the purine and pyrimidine pathways have not been well defined, it has been proposed that either the end products of purine nucleotide synthesis (IMP and ATP) or PP-ribose-P, a rate-limiting reactant for purine synthesis, may play a role in controlling the activity of carbamyl phosphate synthetase II.

Another observation of significance regarding the use of AICAriboside to enhance nucleotide synthesis is the finding that infusion of this riboside at the rate of 0.19 mmol/min did not lead to significant changes in heart rate, systemic blood pressure, cardiac output, or regional myocardial blood flow. Thus, unlike adenosine administration, which leads to profound changes in the hemodynamic status of the animal, AICAriboside may be administered in doses large enough to increase the rate of purine nucleotide synthesis without deleterious effects on the cardiovascular system.

EXAMPLE 2

In Vivo Repletion of ATP and GTP Pools in Postischemic Myocardium

EXPERIMENTAL PROCEDURES

Catheters were placed in the left atrium and aorta, and a snare positioned around the left anterior descending coronary artery in 15 open-chest dogs. Regional myocardial blood flow was measured and transmural tissue samples were obtained using known techniques. Blood flow measurements and tissue samples were obtained prior to and just before release of a 12-minute coronary occlusion. The chest was closed and the animals allowed to awaken. Twenty-four hours later, the animals were anesthetized, the chest opened, blood flow measured, and tissue samples obtained. No hemodynamic measurements were made on the animals.

In seven animals, 200 mM AICAriboside (Sigma Chemical Co.) was infused into the left atrial catether at either 14 $\mu$mol/min ($n=2$) or 37 $\mu$mol/min ($n=5$) beginning with coronary occlusion and continuing for 24 hours. Eight control animals were infused with an equal volume of saline over 24 hours.

Nucleotide and creatine phosphate analyses were performed by high performance liquid chromatography on acid extracts of the tissue as previously described. Nucleotide analysis is described in Example 1, and creatine phosphate analysis is described in Juengling and Kammermeier, Anal. Biochem., 102, 358-361 (1980).

All comparisons between AICAriboside and saline treated animals were done by unpaired analyses.

Results

There were no differences in regional flow at any time point when the AICAriboside-treated group was compared to the saline group (Table III). The mean ischemic flow in the AICAriboside group was slightly but not significantly higher than the saline group due to one animal with higher ischemic and nonischemic area flows. The presence of a reactive hyperemic response to all animals indicated to mechanical impediment to reperfusion.

TABLE III

Regional Myocardial Blood Flow (mm/min per g) in the AICAriboside and Saline-treated Groups

| | Preocclusion | Occlusion | 24 hr Postischemic | 24 hr Nonischemic |
|---|---|---|---|---|
| AICAriboside | | | | |
| Epicardial | 1.14 ± 0.16 | 0.20 ± 0.08 | 1.07 ± 0.23 | 0.99 ± 0.21 |
| Endocardial | 0.94 ± 0.09 | 0.26 ± 0.14 | 0.98 ± 0.22 | 0.97 ± 0.21 |
| Saline | | | | |
| Epicardial | 1.18 ± 0.04 | 0.11 ± 0.03 | 0.80 ± 0.16 | 0.89 ± 0.16 |
| Endocardial | 1.05 ± 0.05 | 0.10 ± 0.02 | 0.79 ± 0.10 | 1.00 ± 0.12 |

All values are reported as the mean ± SEM. Comparison of the AICAriboside to saline-treated at each time point revealed no significant differences.

AICAriboside was transported into postischemic cardiac myocytes and phosphorylated as evidenced by the accumulation of 0.069±0.016 and 0.076±0.008 μmol/g at 24 hr of the ribotide of AICAriboside (AICAR) in epicardium and endocardium of the previously isochemic region. No AICAR was detectable in preocclusion samples from either group nor in any of the biopsies obtained from the saline-treated group.

Figure 3B:
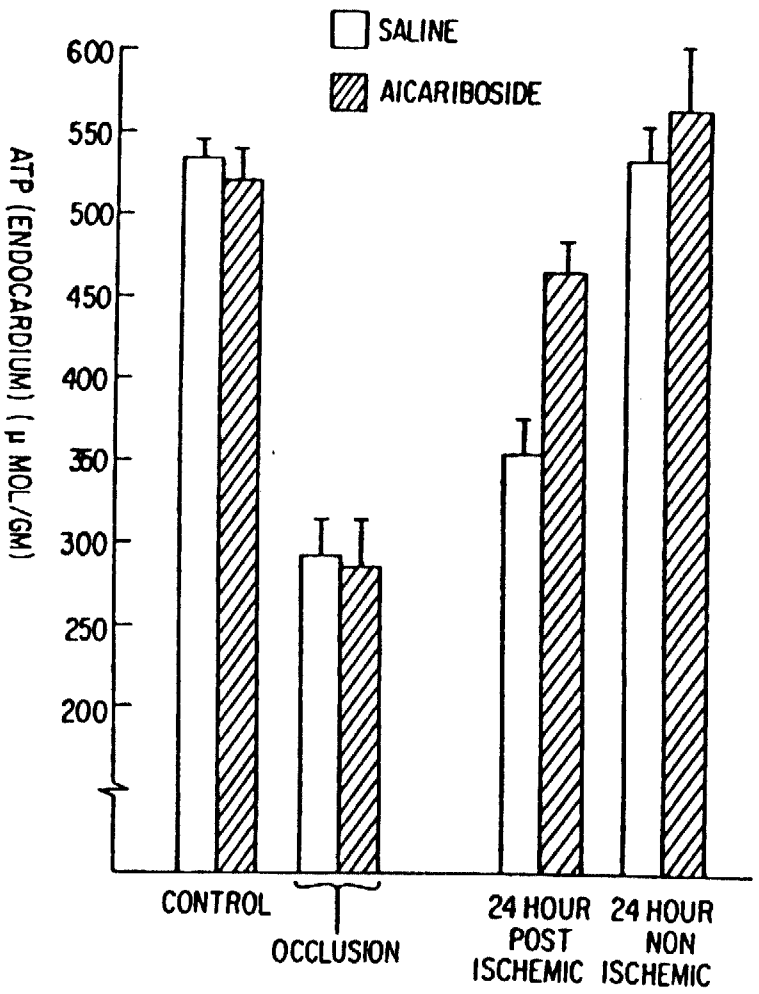
Figure 3A:
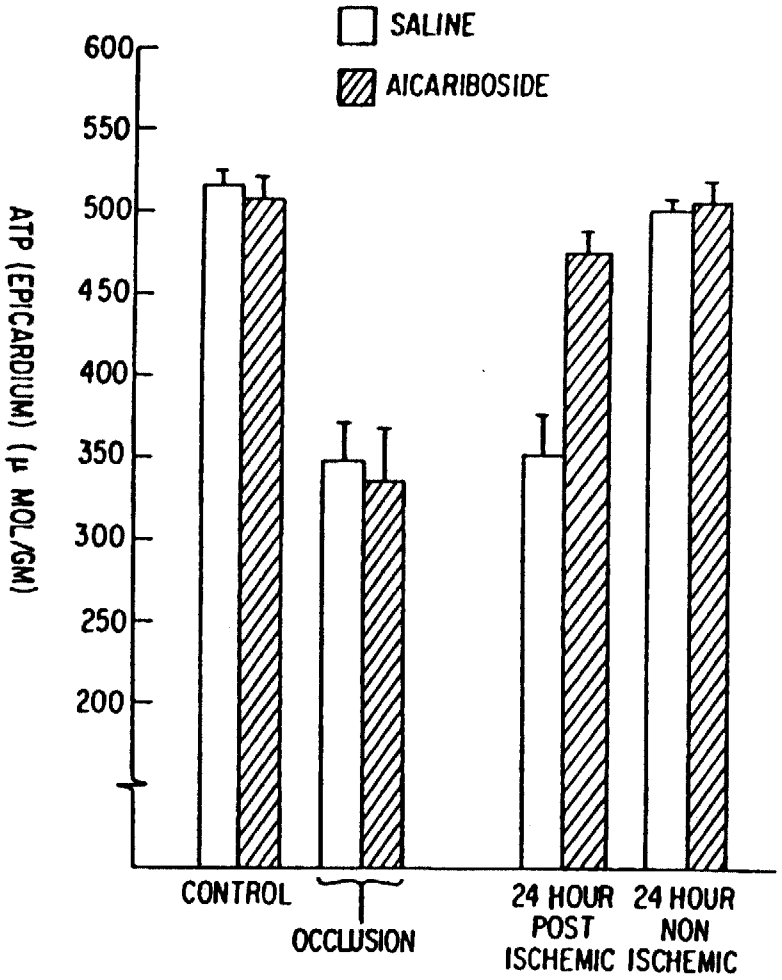

AICAR was metabolized to IMP in postischemic as well as normal myocardium, as evidenced by the 3- to 6-fold increase in IMP at 24 hours in both of these regions in the AICAriboside-treated group (Table IV). IMP content did not change in either the postischemic or nonischemic regions over the course of the study in saline-treated animals (Table IV). The ATP content of myocardium in the AICAriboside and saline-treated groups is shown for all time points in FIG. 3. ATP content of the preocclusion samples and the percentage drop in ATP during ischemia were comparable in both groups. After 24 hours of reperfusion, both the epicardial and endocardial ATP content of the previously ischemic region was greater in the AICAriboside group when compared to the saline-treated animals ($P<0.001$). This represents a 41% (epi) and 63% (endo) increase in the AICAriboside group compared with only a 2% (epi) and 21% (endo) increase in the saline-treated group. Total adenine nucleotide content (ATP+ADP+AMP) of the postischemic region was also greater in the AICAriboside group with no detectable differences in AMP or ADP content between the two groups (Table IV).

Figure 4B:
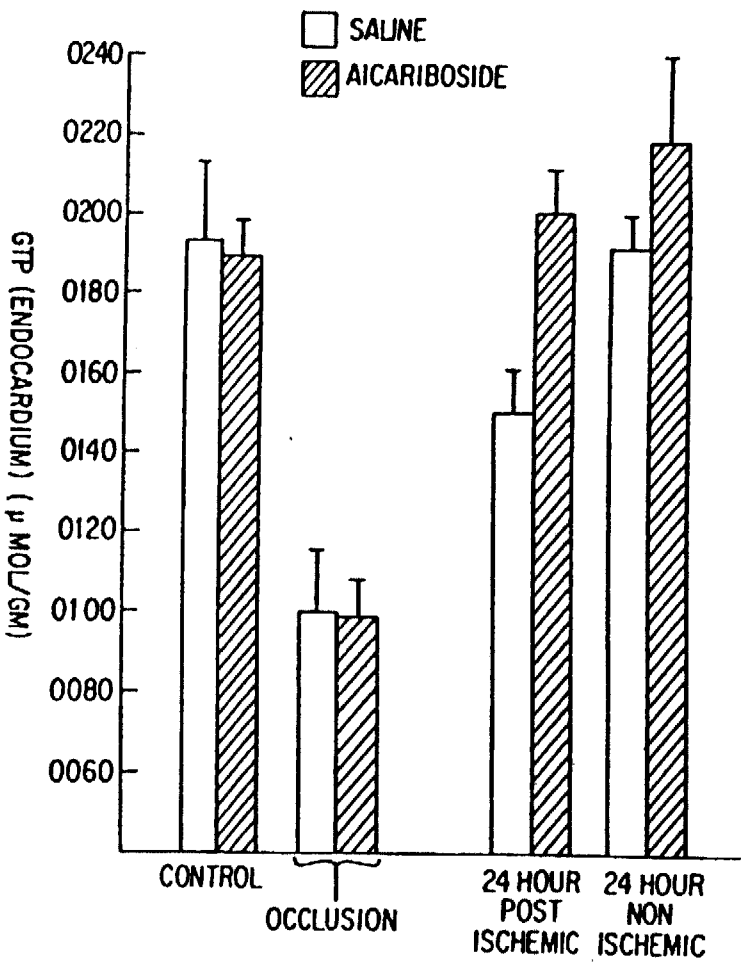
Figure 4A:
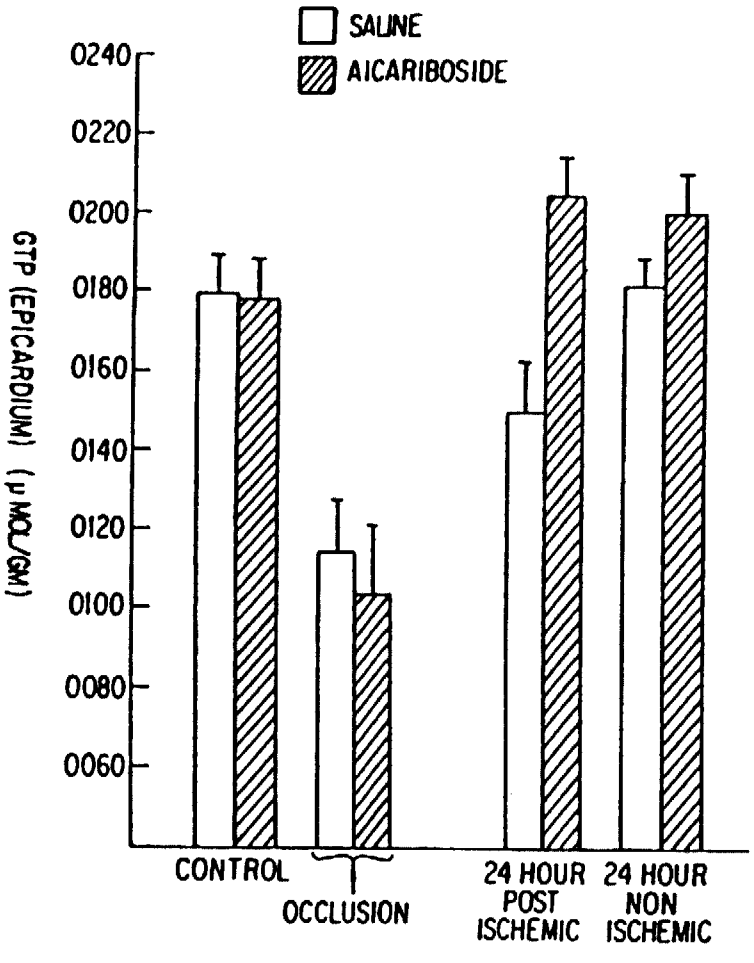

Changes in the GTP pools parallel those seen in the ATP pools (FIG. 4). After 24 hours of reperfusion, the GTP content of the previously ischemic region was greater in the AICAriboside group in both the epicardium and endocardium ($P<0.003$) when compared with the saline-treated group. GTP content was restored to nonischemic levels in the AICAriboside group, while guanine nucleotide pool remained depressed at 82% (epi) and 78% (endo) of nonischemic levels in the saline-treated group.

It is less clear whether AICAriboside administration had any effect on the rate of repletion of the pyrimidine and pyridine nucleotide pools in postischemic myocardium because of the more rapid rate of repletion of both these classes of nucleotides, relative to that of the purine nucleotides, in the saline-treated group (Table IV). There were no statistically significant differences between the two groups with respect to UTP, CTP, or $NAD^+$ content of myocardium from the postischemic region.

Creatine phosphate content fell to a comparable extent at the end of occlusion in both groups and was restored to preocclusion levels in the postischemic regions in both groups (Table IV).

Discussion

Example 1 demonstrates that AICAriboside and the remaining compounds of the invention are taken up rapidly by myocardial cells and readily phosphorylated and metabolized to purine nucleotides in these cells. One advantage offered by this precursor is that it enters the do novo pathway distal to the critical regulatory reactions and consequently, it can markedly increase the rate of purine nucleotide synthesis. In animals with normal myocardial nucleotide pools, there is limited expansion of the ATP and GTP pools following AICAriboside administration, the majority of newly

TABLE IV

Myocardial Nucleotide and Creatine Phosphate Content (μmol/g wet wt) in the AICAriboside and Saline-treated Groups

| | Preocclusion | | Occlusion | | 24 Hr postischemic | | 24 Hr postischemic | |
|---|---|---|---|---|---|---|---|---|
| | AICAriboside | Saline | AICAriboside | Saline | AICAriboside | Saline | AICAriboside | Saline |
| AMP epi | 0.064 ± 0.016 | 0.046 ± 0.005 | 0.135 ± 0.045 | 0.162 ± 0.022 | 0.048 ± 0.009 | 0.042 ± 0.011 | 0.036 ± 0.005 | 0.043 ± 0.004 |
| endo | 0.066 ± 0.007 | 0.065 ± 0.010 | 0.089 ± 0.012 | 0.130 ± 0.016 | 0.056 ± 0.019 | 0.033 ± 0.008 | 0.041 ± 0.005 | 0.044 ± 0.004 |
| ADP epi | 0.87 ± 0.03 | 0.74 ± 0.05 | 0.99 ± 0.11 | 1.07 ± 0.08 | 0.73 ± 0.05 | 0.60 ± 0.05 | 0.70 ± 0.05 | 0.72 ± 0.05 |
| endo | 0.92 ± 0.03 | 0.82 ± 0.06 | 0.86 ± 0.06 | 0.86 ± 0.08 | 0.78 ± 0.09 | 0.60 ± 0.06 | 0.75 ± 0.07 | 0.74 ± 0.04 |
| CTP epi | 0.056 ± 0.004 | 0.057 ± 0.002 | 0.023 ± 0.003 | 0018 ± 0.003 | 0.051 ± 0.004 | 0.046 ± 0.003 | 0.051 ± 0.005 | 0.050 ± 0.002 |
| endo | 0.055 ± 0.001 | 0.060 ± 0.003 | 0.016 ± 0.003 | 0.023 ± 0.014 | 0.052 ± 0.005 | 0.045 ± 0.002 | 0.056 ± 0.004 | 0.056 ± 0.004 |
| UTP epi | 0.122 ± 0.005 | 0.126 ± 0.005 | 0.061 ± 0.007 | 0.051 ± 0.004 | 0.104 ± 0.121 | 0.107 ± 0.007 | 0.096 ± 0.008 | 0.115 ± 0.008 |
| endo | 0.132 ± 0.004 | 0.134 ± 0.007 | 0.055 ± 0.007 | 0.039 ± 0.007 | 0.121 ± 0.013 | 0.116 ± 0.010 | 0.106 ± 0.011 | 0.122 ± 0.009 |
| NAD epi | 0.060 ± 0.02 | 0.65 ± 0.02 | 0.47 ± 0.03 | 0.53 ± 0.02 | 0.56 ± 0.03 | 0.53 ± 0.03 | 0.55 ± 0.02* | 0.62 ± 0.01 |
| endo | 0.058 ± 0.04 | 0.65 ± 0.02 | 0.45 ± 0.02 | 0.52 ± 0.02 | 0.57 ± 0.02 | 0.56 ± 0.02 | 0.60 ± 0.05 | 0.65 ± 0.01 |
| CP epi | 7.7 ± 0.6 | 7.8 ± 0.5 | 2.9 ± 0.7 | 1.6 ± 0.3 | 7.1 ± 0.5 | 7.6 ± 0.9 | 7.8 ± 0.5 | 6.9 ± 0.4 |
| endo | 6.8 ± 0.7 | 7.0 ± 0.2 | 2.0 ± 0.3 | 1.1 ± 0.2 | 7.8 ± 1.1 | 8.6 ± 1.1 | 6.9 ± 0.5 | 7.0 ± 0.6 |
| IMP epi | 0.005 ± 0.002 | 0.004 ± 0.006 | 0.007 ± 0.001 | 0.006 ± 0.001 | 0.025 ± 0.007* | 0.003 ± 0.007 | 0.015 ± 0.004* | 0.002 ± 0.001 |
| endo | 0.004 ± 0.001 | 0.001 ± 0.001 | 0.008 ± 0.002 | 0.004 ± 0.001 | 0.027 ± 0.007* | 0.005 ± 0.001 | 0.017 ± 0.004* | 0.004 ± 0.001 |

All values are reported as the mean ± SEM.
*Indicates $P < 0.05$ when AICAriboside compared to saline group.

synthesized IMP being diverted out of the cell through catabolic pathways. In the present in vivo study, it is demonstrated that this purine precursor is capable of enhancing the rate of repletion of the ATP and GTP pools in postischemic myocardium.

AICAriboside has additional properties which are useful in delineating the mechanism by which it enhances the rate of repletion of the ATP and GTP pools. The finding that the AICAR and IMP content of the myocardium increases after AICAriboside administration establishes the increased availability of precursors for ATP and GTP synthesis these cells. This, coupled with the finding of an enhanced rate of repletion of the ATP and GTP pools following AICAriboside of administration, documents that limited availability of purine precursor is responsible for the prolonged period required for repletion of these nucleotide pools in postischemic myocardium and provides a precursor suitable for promoting the desired repletion.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States:

[1. A method of increasing the rate of repletion of adenosine triphosphate and guanosine triphosphate nucleotides in a tissue deficient in said nucleotides, which comprises:

administering to said tissue a therapeutically effect amount of 5-amino-4-imidazolecarboxamide riboside or a pharmaceutically acceptable salt thereof sufficient to increase the rate of said repletion.]

[2. The method of claim 1, wherein said amount is from 0.1 to 2.0 μmole/min/kg.]

[3. The method of claim 1, wherein said amount is from 0.2 to 1.0 μmole/min/kg.]

[4. The method of claim 1, wherein said compound is 5-amino-4-imidazolecarboxyamide riboside.]

[5. The method of claim 4, wherein the amount of said compound is from 0.2 to 1.0 μmole/min/kg.]

[6. The method of claim 1, wherein said administering is to a tissue in a human.]

[7. The method of claim 6, wherein said tissue is myocardial tissue.]

[8. The method of claim 7, wherein said compound is administered in an amount of from 0.2 to 1.0 μmole/min/kg.]

[9. The method of claim 1, wherein said administering is to a tissue maintained outside a human or animal body.]

[10. The method of claim 9, wherein said amount is from 0.1 to 2.0 μmole/min/kg.]

[11. The method of claim 9, wherein said amount is from 0.2 to 1.0 μmole/min/kg.]

[12. The method of claim 9, wherein said compound is 5-amino-4-imidazolecarboxamide riboside.]

[13. The method of claim 12, wherein the amount of said compound is from 0.2 to 1.0 μmole/min/kg.]

[14. The method of claim 9, wherein said tissue comprises part of a human organ.]

[15. The method of claim 14, wherein said organ is a kidney, heart, liver, or pancreas.]

[16. The method of claim 1, wherein said administering is to a human afflicted with Lesch-Nyhan Syndrome.]

*17. A method of treating an ischemic condition in a human comprising the step of administering a therapeutically effective amount of 5-amino-4-imidazolecarboxamide riboside or a pharmaceutically acceptable salt thereof during and after ischemia wherein said ischemic condition is a myocardial ischemia.*

*18. A method comprising the administration of a therapeutically effective amount of 5-amino-4-imidazolecarboxamide riboside during coronary bypass surgery in a human.*

*19. A method of treating an ischemic condition in a human comprising the step of administering a therapeutically effective amount of 5-amino-4-imidazolecarboxamide riboside or a pharmaceutically acceptable salt thereof during and after ischemia wherein said ischemic condition is a myocardial ischemia caused by a coronary occlusion.*

*20. A method of treating an ischemic condition in a human comprising the step of administering a therapeutically effective amount of 5-amino-4-imidazolecarboxamide riboside or a pharmaceutically acceptable salt thereof during and after ischemia wherein said ischemic condition is a myocardial ischemia caused by a myocardial infarction.*

*21. A method of treating an ischemic condition in a human comprising the step of administering a therapeutically effective amount of 5-amino-4-imidazolecarboxamide riboside or a pharmaceutically acceptable salt thereof during and after ischemia wherein said ischemic condition is angina.*

*22. A method of treating an ischemic condition in a human comprising the step of administering a therapeutically effective amount of 5-amino-4-imidazolecarboxamide riboside or a pharmaceutically acceptable salt thereof during and after ischemia wherein said myocardial ischemia is caused by a coronary occlusion and wherein said 5-amino-4-imidazolecarboxamide riboside is administered following thrombolysis for said coronary occlusion.*

* * * * *